United States Patent [19]

Campbell

[11] 4,321,917

[45] Mar. 30, 1982

[54] SURGICAL DRAPE SUPPORT AND OXYGEN SUPPLY DEVICE

[76] Inventor: William H. Campbell, 1411 W. Fourth St., Coffeyville, Kans. 67337

[21] Appl. No.: 171,437

[22] Filed: Jul. 23, 1980

Related U.S. Application Data

[63] Continuation-in-part of Ser. No. 40,087, May 17, 1979, abandoned.

[51] Int. Cl.3 .............................................. A61M 16/02

[52] U.S. Cl. .......................... 128/205.26; 128/200.24; 128/204.18; 248/445; 248/124

[58] Field of Search ......... 128/132 D, 200.24, 204.18, 128/205.26, 202.18, 202.13, 33, 20, 3, 325; 5/503, 505, 507, 512, 163, 414, 508; 248/445, 124, 279; 269/322, 323, 325, 328

[56] References Cited

U.S. PATENT DOCUMENTS

| | | | |
|---|---|---|---|
| 1,211,527 | 1/1917 | Berndt | 248/279 |
| 1,257,332 | 2/1918 | Erlandson | 5/505 |
| 1,862,237 | 6/1932 | Pepler | 248/279 |
| 2,180,480 | 11/1939 | Richardson | 128/200.24 |
| 2,290,437 | 7/1942 | Kilgore et al. | 128/200.24 |
| 2,628,803 | 2/1953 | Krewson | 248/124 |
| 2,994,501 | 8/1961 | Barnard | 248/279 |
| 3,464,411 | 9/1969 | Martinez | 128/202.18 |
| 3,530,515 | 9/1970 | Jacoby | 128/205.26 |
| 3,859,993 | 1/1975 | Bitner | 128/200.24 |
| 3,877,691 | 4/1975 | Foster | 269/322 |

FOREIGN PATENT DOCUMENTS

| | | | |
|---|---|---|---|
| 807407 | 1/1959 | United Kingdom | 128/200.24 |

*Primary Examiner*—Henry J. Recla

*Attorney, Agent, or Firm*—LeBlanc, Nolan, Shur & Nies

[57] ABSTRACT

A surgical drape support device for use with a cover sheet and a conduit for supplying oxygen to a patient disposed on a surgical operating table. The device has a base member which is inserted between a mattress and the surgical table and a support rod which has a drape arm for disposition over a patient. The drape arm can also function as an oxygen distribution means. The base member and the support rod are interconnected by a unitary adjustment means which provides for at least four degrees of adjustment motion for the drape support arm. All adjustments to control the positioning of the drape arm are made from a location removed from the operating field and the patient and are made without removing the overlying drape which is used to retain an oxygen atmosphere over the patient's nose and mouth. One of the degrees of adjustment motion is over an arc about a longitudinal axis which is located parallel to and closely spaced from the edge of the operating table in order to allow movements of the patient's head to be followed.

34 Claims, 4 Drawing Figures

SURGICAL DRAPE SUPPORT AND OXYGEN SUPPLY DEVICE

RELATED APPLICATIONS

The present application is a continuation-in-part of the inventor's copending application Ser. No. 40,087, filed May 17, 1979 and now abandoned. The disclosure of that application is hereby incorporated by reference as though fully set forth herein.

BACKGROUND OF THE INVENTION

The present invention relates to a device for supporting a surgical drape above a patient and enabling the supplying of a respirable atmosphere to a patient during a surgical operation. The atmosphere may be either an oxygen enriched air or pure oxygen. The device is used in conjunction with a surgical operating table having a patient supporting mattress thereon and with a drape or cover sheet in order to retain the supplied atmosphere for patient respiration. The drape support device described herein is of particular usefulness with respect to ophthalmological operations in which a surgical field must be maintained through an opening in a drape for operations upon the eye.

Intraocular operations upon the human eye are mostly conducted under a local anesthetic and hence the patient is awake and must be kept comfortable during the operation. Movement to a new patient position must be provided for under the direction of the operating ophthalmologist. It is desirable to let the patient seek the most comfortable attitude and to then arrange the cover drape so that the patient's breathing can be natural and unencumbered. At the same time, another major requirement is that the operating microscope field must be well presented for access by the ophthamologist. Yet another requirement is that the field be presented in a manner so that operating tools can be moved in and out without obstruction. The operating field must be maintained directly centered on the eye since a small field aperature in the drape is used to prevent the patient from looking up at the surgeon with the other eye and to maintain sanitary field conditions. Also the drape support device must be rigid once fixed in position so that accidental movement during an operation is rendered impossible. Operating room personnel often rest their hands and place various instruments on the drape. These requirements mean that the various devices and surgical implements are close spaced to the operating field which is small and delicate to properly maintain.

These critical and desirable conditions are regarded as important for intraocular surgical procedures such as cataracts extractions with or without lens implants, glaucoma treatment, corneal transplants (keratoplasties), retinal detachment treatment and exploratory orbitotomies for tumor and bone chip location. Patient comfort is less of concern for those extraocular procedures where general anesthetics are used such as for eyelid plastic surgery, strabismus (eye muscle surgery) procedures, refractive radial keratotomies procedures, and retinal surgery.

One aspect of the criticality of the spacing is that the cover sheet which is used to maintain a respirable atmosphere over the patient's nose and mouth must not be lifted or moved off of the underlying drape support device. Movement of the cover sheet is necessary in many of the devices in the prior art because the adjustment screws on those devices are located at various positions which underly the drape or cover sheet. Another general problem in the prior art is that the adjustments necessary to obtain different positions of the atmosphere supply device and the overlying cover sheet are distributed at different locations rather than being located in a single position outside of the cover sheet. Such devices require a special search for the proper set screw which then disturbs the delicate surgical procedure.

Another problem in surgical operations in which close control must be maintained over the operating field is that the underlying support device for the cover sheet should be capable of being dipped downwardly toward the patient in an arcuate motion which will folow the turn of a patient's head as the patient tries to maintain an acceptable level of comforture during the eye operation which can frequently be one hour to one and one half hours in duration.

Maintaining patient comfort can best be provided in head and neck operations by holding the cover drape a substantial distance of 5 cm to 10 cm above the patient's nose and mouth and by supplying a distributed flow of oxygen which gives a sensation of air flow across the face. This helps to alleviate apprehension arising from a mild suffocation sensation which can lead to a dyspneic (shortness of breath) condition in some patients. The oxygen flow provided reassures the patient and permits better surgery results.

U.S. Pat. No. 2,180,480 to M. G. Richardson illustrates some of the above problems. The set screws which allow adjustment of the anesthetics screen support frame immediately underlie the cover screen and hence it is necessary to lift the drape off of the support in order to adjust the same to various positions. Also in this device, there is no provision for the inflow of oxygen.

U.S. Pat. No. 3,347,544 to Uffenorde discloses a head rest for eye surgery having a nonadjustable anesthetic screen support attached thereto. The fixed position of this type of device has been found to be unacceptable. U.S. Pat. No. 3,482,571 to Behrendt shows a similar head rest with an oxygen tube support means.

U.S. Pat. No. 2,628,803 to Krewson shows an anesthetic screen support device for use during eye surgery in which the set screws are covered over by the screen material. Also, in this device it is not possible to follow the patients head movements since no single adjustment motion permits following of the turning of a patient's head.

U.S. Pat. No. 2,290,437 to Kilgore et al shows a support structure for use in eye operations. The upper thumb screw can only be adjusted by removing the overlying screen material. The gas supply tube is not supported for making an arcuate motion inward and outward toward and away from the patient and there is no provision for distribution of the gas flow over the patient's face. U.S. Pat. No. 3,530,515 to B. Y. Jacoby shows a patient guard for use during eye surgery which presents problems similar to the Kilgore device as does the device shown in German Pat. No. 2,614,202.

U.S. Pat. No. 2,963,247 to G. L. Collier et al. shows a form of an endotracheal tube holder which is not functional for eye operations or for supporting a drape.

U.S. Pat. No. 3,877,691 to Foster shows a flexible arm anesthetic shielding device which does not support a cover drape, supply oxygen nor provide the required rigidity of support for ophthalmological operations.

U.S. Pat. No. 3,859,993 to Bitner shows a largely nonadjustable oxygen supply and drape sheet for eye surgery in which the oxygen flows too far from the patient's face to alleviate a suffocation sensation.

Other medical and/or surgical devices having various types of positioning adjustments are disclosed in U.S. Pat. Nos. 3,026,079, 3,625,219 and 3,881,477. British Pat. No. 807,407 published Jan. 14, 1959 also shows an anesthetic gas supply tube and an adjustable support therefore.

SUMMARY OF THE INVENTION

A surgical drape support device is provided for use with a cover sheet and a conduit for supplying a respirable gas mixture to a patient disposed on a mattress overlying a surgical operating table. The device has a base member which is inserted between the mattress and the surgical table and a support rod which has a drape arm for disposition over a patient. This drape arm can also function as an oxygen distribution means by provision of an associated gas supply conduit. The base member and the support rod are interconnected by a unitary adjustment means which provides for at least 4 degrees of adjustment motion for the drape arm of the support rod. All adjustments for positioning of the drape arm can be made conveniently at the side of the operating table from a location which is removed from the operating field and the patient. All of the position adjustments can be made without removing the overlying drape or cover sheet which is used to retain the respirable atmosphere in the vicinity of the patient's nose and mouth.

One of the degrees of adjustment motion is over an arc about a longitudinal axis which is located parallel to and closely spaced from the edge of the operating table in order to allow movement of the drape arm toward and away from the patient on the operating table to provide for different side positions of the patient's head.

The unitary adjustment means is positioned on the drape support device near the edge of the operating table and is in the form of a block having adjustment means cooperating therewith which enable fixing of the relative position of the base member and the drape arm in various positions provided by the four degrees of adjustment motion.

It is, therefore, an object of the present invention to provide a drape support having a respirable atmosphere supply capability for use on surgical tables in which position adjustments can be achieved without removing the overlying cover sheet which is supported by said device.

Another object of the present invention is to provide a drape support and respirable atmosphere supply device wherein a drape arm is moveable in at least four degrees of adjustment motion which are all controlled from a unitary adjustment means which is positioned outside of the operating field and the cover sheet.

Another object of the present invention is to provide an improvement in a surgical drape support device of the above type in which a unitary adjustment means is interconnected between a base member and a support rod in order to provide at least four degrees of adjustment motion for a drape arm of the support rod.

The drape support device described and claimed herein is also useful in a wide range of surgical and other medical procedures. For example, in addition to eye surgery it is useful in ear, nose and throat; dermatological; plastic or facial reconstruction; and head and neck operations. More special employments are for the supply of oxygen to burned areas in skin grafting procedures to prevent anerobic infections of the gangrene type or as a supplementary oxygen tent with a transparent cover sheet. In abdominal and chest surgery the device can be used to protect against accidental closing off the anesthetic (endotracheal) tube.

Specific preferred embodiments of the invention will be described below with reference to the appended drawing figures.

DESCRIPTION OF THE PREFERRED EMBODIMENTS

Figure 1:
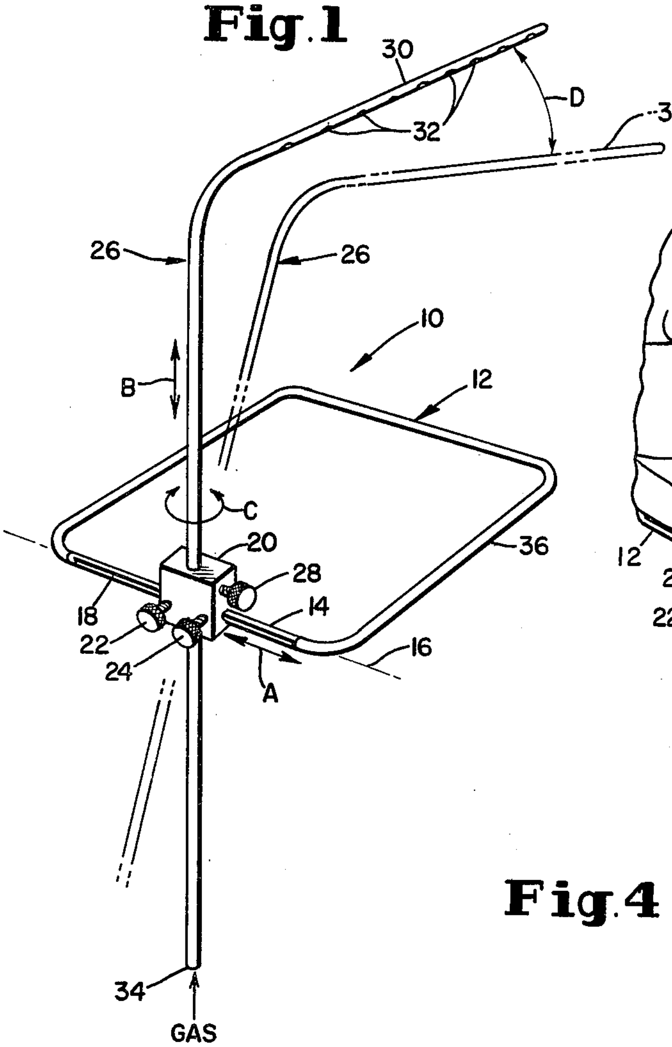
FIG. 1 is a perspective view of the drape support and respirable atmosphere supply device in accordance with the present invention.
Figure 2:
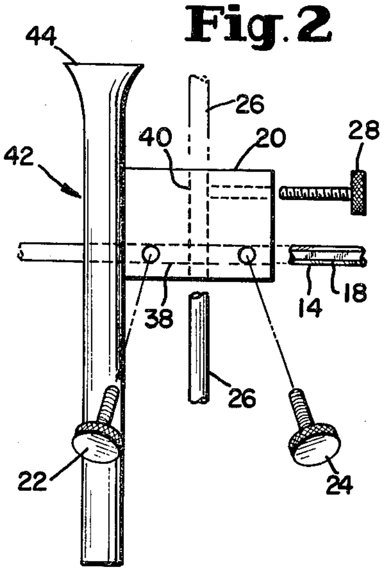
FIG. 2 is a front plan view of the unitary adjustment means of the support device showing the knurled set screws removed therefrom.

Referring to FIGS. 1 and 2, a surgical drape support device 10 is shown with a base member 12 which is in the form of a generally rectangular metal frame having a rail 14 integrally formed by one side thereof. Rail 14 has a longitudinal axis 16 which is disposed along the longitudinal edge of an operating table as described below. This rail 14 also has a flat 18 along the outer surface thereof.

Rail 14 has a unitary adjustment block 20 slidably and rotatably supported thereon. Knurled set screw 22 is provided in adjustment block 20 in order to clamp against the outside surface of rail 14 to secure block 20 against the sliding and rotating motions. Set screw 22 abuts flat 18 on rail 14 when the adjustment block 20 is in the vertical position shown in FIG. 1. If desired, a secnd knurled set screw 24 can be provided in adjustment block 20 for allowing greater gripping force to be exerted upon the rail 14.

Adjustment block 20 has a vertical passage therein which accommodates a support rod 26 for vertical sliding adjustment and rotating adjustment. A knurled set screw 28 is provided on the side of unitary adjustment block 20 to fix the position of rod 26 with respect to the block 20. Support rod 26 has a drape arm 30 connected to its upper end and disposed generally perpendicularly thereto so as to form a horizontally disposable part thereof. This drape arm 30 can preferrably have a series of apertures 32 located therealong in the under surface in order to provide for the outflow of a respirable atmosphere gas from a conduit formed within the drape arm. The preferred embodiment is to form support rod 26 and drape arm 30 from a continuous metal tube. The opposite end of the support rod 26 can then have a receiving opening 34 which can be connected to a source of respirable gas which is provided in the operating theater. An oxygen flow of about 6 liters/minute is normally used.

The drape arm 30 of support rod 26 is then adjustable along four degrees of adjustment motion denoted as A–D in FIG. 1. Knurled set screws 22 and 24 provide securing means against sliding motion A with respect to rail 14 as well as against rotating motion about longitudinal axis 16 which then produces an arcuate motion D about this longitudinal axis 16 in order to obtain a movement of drape support arm 30 toward and away from a patient underlying the drape arm. If desired, the two set screws 22 and 24 can be replaced with a single set screw having a leverage means affixed to the outer end such as a large knob with finger scallops or an operator lever.

Two other degrees of adjustment motion for drape arm 30 are the vertical motion B and the rotating motion C. These two motions are controlled and secured against by means of knurled set screws 28. The arcuate adjustment motion D about the longitudinal axis 16 of rail 14 allows for various angular positions as shown in phantom lines away from the horizontal position for the drape arm 30. The material of construction for all of the parts of the supplied device 10 can be a metal such as stainless steel or other easily cleaned material such as rigid polymeric materials. Due to the requirement for rigidity during an operation, an all metal construction is preferred.

Base member 12 can be constructed of a tubular frame portion 36 which is secured to either end of a solid metal rail 14 after that rail is inserted through an opening 38 in the unitary adjustment block 20. The support rod 26 can then be placed into the unitary block 20 through the vertical opening 40 therein. The openings 38 and 40 can be seen in FIG. 2. These two openings are spaced from one another within unitary block 20 so that the rail 14 does not contact gas tube 26. If desired, the corners and edges of unitary block 20 can be beveled for safety. FIG. 2 also illustrates the optional element of an air exhaust tube 42 which is preferrably attached to the side of adjustment block 20. The exhaust tube 42 has an enlarged upper intake port 44 through which the heavier density carbon dioxide exhaled by the patient can flow. This exhaust tube can be circular or rectangular in cross-section and can be removably attached to block 20.

Figure 3:
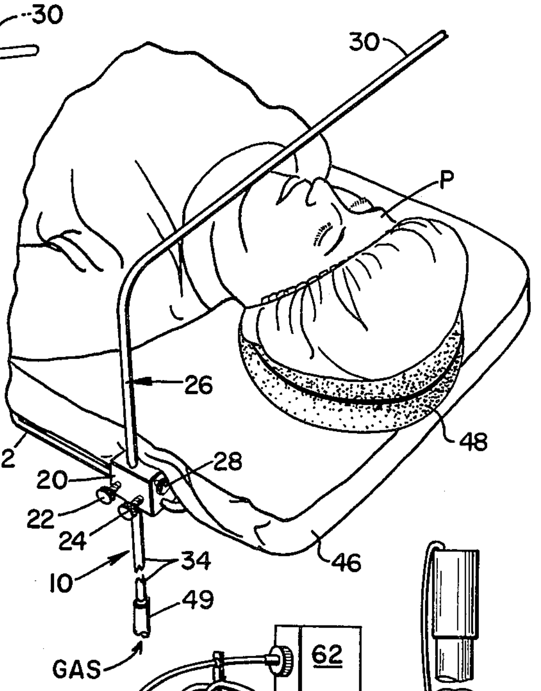
FIG. 3 shows a schematic perspective view of the drape support device in use on an operating table with a patient.

Referring now to FIG. 3, supply device 10 is shown having the base member 12 underlying a mattress 46 which is positioned with the exhaust tube 42 removed on an operating table (not shown). A patient P is supported on the operating table with a head rest 48. The drape arm 30 which also functions as a gas distribution means is positioned to overlie the patient and is secured in the positin shown by adjustment of knurled set screws 22, 24 and 28 on unitary adjustment block 20. The opposite end of the hollow support rod 26 has the receiving opening 34 connected to a gas hose 49 for the supply of a respirable gas.

When the drape arm and gas distribution portion 30 is aligned horizontally as shown in FIG. 3, the knurled set screws 22 and 24 abut the flat 18 on rail 14. However, when it is necessary to adjust this drape arm 30 to the angular position shown by phantom lines in FIG. 1, the knurled knobs 22 and 24 are tightened down upon the round portion of rail 14. Both of set screws 22 and 24 are then desirable to secure the gas distribution portion 30 in a fixed off-vertical position when this angular adjustment about arc D as shown in FIG. 1 is used.

Figure 4:
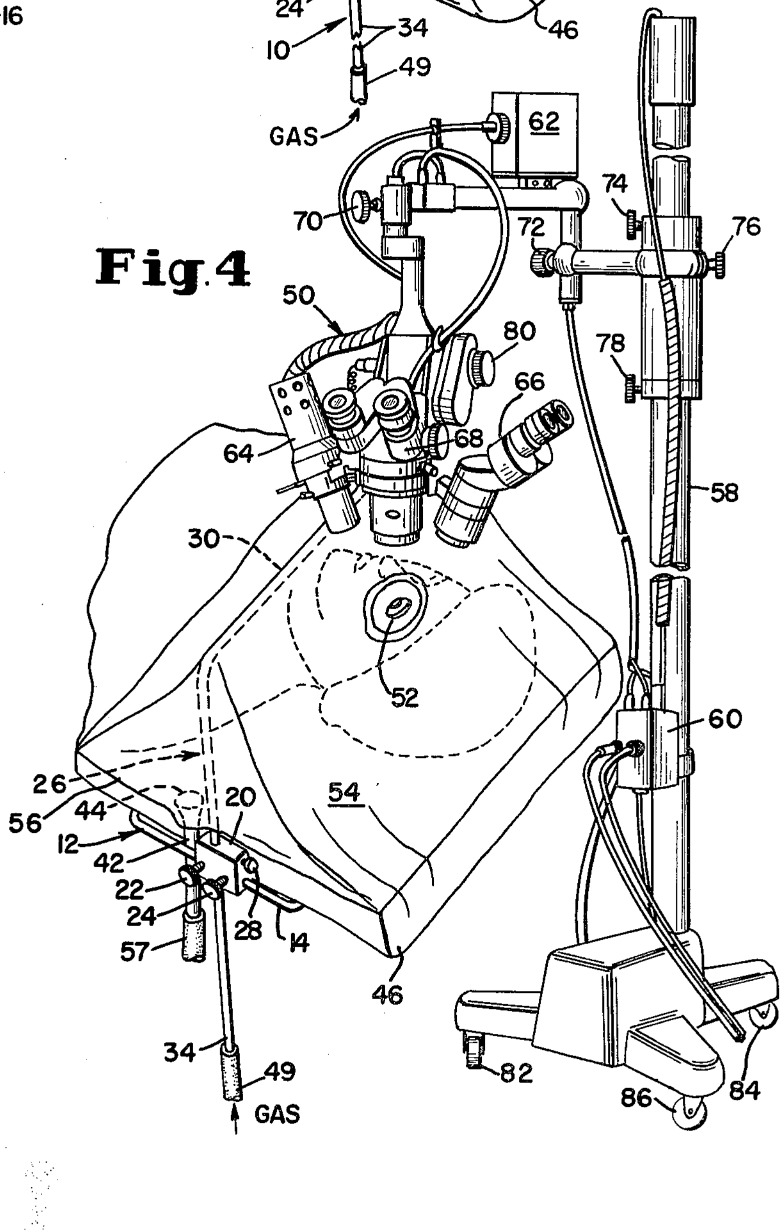
FIG. 4 shows the use of the support device for supporting an overlying cover sheet which provides an operating field viewable through an operating ophthalmological microscope.

FIG. 4 shows a schematically depicted operating ophthamological microscope 50 positioned over an operating field 52 which is formed by an opening in a drape or cover sheet 54 which is supported by drape arm 30. An angle of about 120° is present at the apex of the supported drape. It can be seen that the edge 56 of the cover sheet can be positioned with respect to the operating table so that the unitary adjustment block 20 is exposed for convenient adjustment by the operating ophthamist without the necessity of moving the cover sheet 54. These adjustments can be made at the beginning of the operation, which is preferable, and also during the often lengthy operations on the eye when patient comfort must be maintained. The four degrees of adjustment motion provided by adjustment means 20 allow patient movements to be accomodated for and still maintain a fully usable operating field 52. This is provided by the four degrees of adjustment motion of the drape arm with respect to the base member 12 and rail 18. An exhaust tube 42 is also shown attached to a flow tube 57 for carrying exhaled gas away from the space under cover sheet or drape 54.

Support device 10 can be used with all operating microscopes such as shown by microscope 50. These microscopes are highly specialized for different types of operations on the head, neck, eyes, ears and throat. An adjustable height floor stand 58 is provided with electrical connections 60 for powering one or more illuminators such as a coaxial illuminator 62 and an oblique illuminator 64 to produce a better viewable operating field 52. It is usual that two or more binocular microscopes 66 and 68 are provided for multiple surgeon use. Other attachments (not shown) can be film and TV cameras. Adjustment knobs 70-80 and brakable wheels 82-86 are typically provided. Slightly different constructions are used for throat, brain and plastic surgery.

The knurled set screw 28 is shown on the front face of the adjustment block 20 in FIGS. 1, 3 and 5. It is also possible to position this set screw 28 on the same surface as the outer set screws 22 and 24. Also, another variation is that only a single set screw engaging rail 14 is necessary if an additional tightening means is provided by means of a mechanical leverage device. That is, knurled set screw 24 is optional.

By FIGS. 3 and 4 the nonprotruding form of the unitary adjustment block 20 can be seen. No portion of the adjustment means or the entire device 10 extends more than several centimeters from the operating table. Hence no equipment inconvenience is set up by this device. Also it is highly significant that all adjustments can be made from a noninterfering position removed from the patient area of the table which is defined to be the space above the entire upper table surface.

The tubular base member 12 can also be constructed in the form of a platform such as described and claimed in the inventor's copending Application Ser. No. 40,087, filed May 17, 1979. In this common subject matter variation a rail 14 is fixed along the outside edge of a base plate member and the unitary adjustment block 20 is then mounted on the rail.

The surgical drape or cover sheet can be constructed of a tight woven cloth, usually cotton; a plastic sheet including one with an adhesive on one side; or a paper web.

If a solid support rod 26 and drape arm 30 are used a separate oxygen tube can be taped to one or both of these members to provide an oxygen flow.

The respirable gas supplied can be either oxygen enriched air or pure oxygen.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. In a surgical drape support device for use on a surgical operating table having a mattress thereon, said device having means defining a base member designed for resting upon said table and adapted to be retained thereon by the mattress and having a side portion thereof adapted to extend laterally from said mattress, and having a drape support means comprising a support rod slidably and rotatably secured to said base member, and a drape arm connected to the upper end of said support rod substantially perpendicular thereto; the improvement comprising a unitary adjustment means interconnected between said base member and said support rod; said adjustment means being mounted on said side portion of said base member such that said adjustment means is slidable in two directions along an axis defined by said side portion of said base member and is rotatable in a plane normal to said axis thereof, at least two securing means cooperating with said adjustment means for adjustably securing said adjustment means to said base member and for adjustably securing said support rod to said adjustment means for providing at least four degrees of adjustment motion for said drape arm with respect to said base member from a position removed from the patient area of said table.

2. The improvement according to claim 1, wherein one of said degrees of adjustment motion of said drape arm is over an arc about said axis defined by said side portion of said base member, said part adapted for location parallel to and closely spaced to the edge of the operating table for enabling movement of said drape arm of said support rod toward and away from a patient on an operating table during use thereof.

3. The improvement according to claim 1, wherein said support rod has two degrees of adjustment motion with respect to said unitary adjustment means, one slidable and one rotatable.

4. The improvement according to claim 1, wherein at least one gas supply conduit is associated with said drape arm for enabling the supply of a respirable atmosphere to a patient.

5. The improvement according to claim 1, wherein said conduit is formed internal to said drape arm and said support rod and wherein said drape arm has aperatures located on the underside thereof for distributing the respirable atmosphere to a patient.

6. The improvement according to claim 1, wherein said securing means of said unitary adjustment means are positioned on at least two surfaces of said adjustment means for enabling positioning adjustment of said drape arm with respect to a patient from a noninterfering position away from the patient area of said table.

7. The improvement according to claims 1, 2, 3, 4 or 6, wherein said securing means are knurled set screws engaged in threaded holes in said unitary adjustment means, and wherein at least one of said screws abuts said support rod and where at least one of said screws abuts said base member.

8. The improvement according to claim 1, wherein said unitary adjustment means is in a form of a block having at least two passages therethrough, one for said base member and one for said support rod, and wherein said securing means are affixed to at least two of the outer surfaces of said block.

9. The improvement according to claim 1, wherein said surgical drape support device is constructed of stainless steel.

10. The improvement according to claim 1, wherein said base member is in the form of a rectangular shaped metal frame.

11. The improvement according to claim 1, wherein a gas exhaust tube is attached to said surgical drape support device for enabling the outflow of gas away from said operating table.

12. The improvement according to claim 1, wherein a cover sheet overlies said drape arm and a substantial portion of a patient outside of an operating field, and wherein said drape arm supports said cover means an operative distance above the patient's nose and mouth.

13. A surgical drape support device for use on a surgical operating table having a supporting mattress thereon, comprising: means defining a base member adapted for support by a surgical table and adapted to be retained thereon by an overlying mattress, a rail integrally formed with said base member and having its longitudinal axis disposed for positioning parallel to an edge of said table, a unitary adjustment means mounted on said rail such that said unitary adjustment means is rotatably about and slidable with respect to said rail, a support rod rotatably and slidably mounted to said adjustment means, a drape arm connected to the upper end of said support rod and extending to overlie said base member and at least two securing means cooperating with said unitary adjustment means for adjustably securing said adjustment means to said base member and said support rod to said adjustment means whereby at least four degrees of adjustment motion are provided for said drape arm from a position removed from the patient area of said table.

14. A surgical drape support device according to claim 13, wherein one of said degree of adjustment motion is over an arc about the longitudinal axis of said rail for enabling movement of said drape arm toward and away from a patient on said operating table.

15. A surgical drape support device according to claim 14, wherein an additional securing means is positioned on an outer surface of said unitary adjustment means to secure said drape arm at selected positions along the arc about the longitudinal axis of said rail.

16. A surgical drape support device according to claim 13, wherein said support rod has two degrees of adjustment motion with respect to said unitary adjustment means, one slidable and one rotatable.

17. A surgical drape support device according to claim 13, wherein at least one gas supply conduit is associated with said drape arm for enabling the supply of a respirable atmosphere to a patient.

18. A surgical drape support device according to claim 16, wherein said conduit is formed internal to said drape arm and said support rod and wherein said drape arm has aperatures located on the underside thereof for distributing the respirable atmosphere a patient.

19. A surgical drape support device according to claim 18 wherein said aperatures of said drape arm are spaced a substantial distance away from the nose and mouth of the patient.

20. A surgical drape support device according to claim 17, wherein an external respirable gas supply hose is connected to said gas supply conduit.

21. A surgical drape support device according to claim 17, wherein a source of oxygen enriched air is attached to said gas supply conduit.

22. A surgical drape support device according to claim 13, wherein said securing means of said unitary adjustment means are positioned on at least two surfaces of said adjustment means for enabling positioning adjustment of said drape arm with respect to a patient from a noninterferring position away from the patient area of said table.

23. A surgical drape support device according to claims 13, 14, 16, 17 or 22, wherein said securing means are knurled set screws engaged in threaded holes in said unitary adjustment means, and wherein at least one of said screws abuts said support rod and at least one of said screws abuts said rail of said base member.

24. A surgical drape support device according to claim 23, wherein a third knurled set screw abuts said rail to provide for additional securing force against movement of said drape arm from a given fixed position along the arc about the axis of said rail.

25. A surgical drape support device according to claim 13, wherein said unitary adjustment means is in the form of a block having at least two passages therethrough, one for said rail and one for said support rod, and wherein said securing means are affixed to at least two of the outer surfaces of said block.

26. A surgical drape support device according to claim 13, wherein said rail of said base member is circular in cross-section.

27. A surgical drape support device according to claim 13, wherein said rail has a flat thereon for establishing contact with at least one of said securing means for facilitating the inter-contact therebetween to enable fixing of a preselected angular position of said drape arm of said support rod with respect to said base member.

28. A surgical drape support device according to claim 13, wherein a cover sheet is supported over a patient by said drape arm of said support rod.

29. A surgical drape support device according to claim 13, wherein said support device is constructed of stainless steel.

30. A surgical drape support device according to claim 13, wherein said base member is in the form of a rectangular shaped metal frame.

31. The method of supporting a surgical drape above a patient's head over a surgical operating table and supplying a respirable atmosphere to the patient through the use of a surgical drape support device having a gas supplied conduit associated therewith in which a base member is designed for resting upon the table and is adapted to be retained thereon by an overlying mattress and in which the drape support device has a support rod engaged by the base member and a drape arm connected to the upper end of the support rod for overlying a patient and wherein a unitary adjustment means interconnects the base member and the support rod and provides for rotatable and slidable engagement with respect to the base member and wherein the adjustment means provides for at least four degrees of adjustment motion for the support rod and drape arm with respect to said base member from a position removed from the patient area of the table; the method comprising the steps of:

placing the patient on the mattress overlying the operating table, moving the support rod to overly the patient's mouth and nose by a substantial distance, tightening the adjustment means to secure the support rod in a fixed vertical position with respect to the patient, arranging a cover sheet over the drape arm and the patient's head, exposing an operating field on the patient through an aperature in the cover sheet, supplying a flow of respirable gas atmosphere through the gas supply conduit, adjusting the position of the drape arm with respect to the nose and mouth of the patient depending upon the position of the patient's head and adjusting the vertical position of the support rod with respect to the base member through change in the adjustment means to accomodate for the movement of the drape arm over different vertically disposed arcs about a longitudinal axis formed by a part of the base member located along the edge of the mattress, said adjusting provided for from a position removed from the patient area of the operating table.

32. The method according to claim 31, including the additional steps of:

following movement of the patient's nose and mouth by adjustment of the position of the drape arm by providing at least four degrees of adjustment motion for the drape arm through operation of the unitary adjustment means, and conducting exhaled gas away from the patient area of the table.

33. The method according to claim 31, including the additional step of illuminating the operating field created by the aperature in the cover sheet.

34. The method according to claim 31, wherein said moving step results in positioning of the support rod about 5 cm to 10 cm above the patient's mouth and nose.

* * * * *

UNITED STATES PATENT AND TRADEMARK OFFICE

CERTIFICATE OF CORRECTION

PATENT NO. : 4,321,917

DATED : March 30, 1982

INVENTOR(S) : William H. Campbell

It is certified that error appears in the above—identified patent and that said Letters Patent is hereby corrected as shown below:

Column 1, line 41, change "aperature" to read --aperture--.

Column 2, line 16, change "folow" to read --follow--.

Column 3, line 4, change "sheet" to read --support--.

Column 4, line 45, change "secnd" to read --second--.

Column 5, line 49, change "positin" to read --position--.

Column 7, lines 51-52, change "aperatures" to read -- apertures-

Column 8, line 61, change "16" to read --17--;

line 63, change "aperatures" to read --apertures--;

line 66, change "aperatures" to read --apertures--.

Column 10, line 23, change "aperature" to read --aperture--;

line 49, change "aperature" to read --aperture--.

Signed and Sealed this

***Thirty-first* Day of *August 1982***

[SEAL]

*Attest:*

GERALD J. MOSSINGHOFF

*Attesting Officer* *Commissioner of Patents and Trademarks*